(12) United States Patent
Hjorth (10) Patent No.: US 12,091,633 B2
(45) Date of Patent: Sep. 17, 2024

(54) PROCESS FOR DRY FRACTIONATION TO OBTAIN A FINAL HARD PALM OIL MID FRACTION

(71) Applicant: AAK AB (PUBL), Malmö (SE)

(72) Inventor: Jeppe Lindegaard Hjorth, Arhus N (DK)

(73) Assignee: AAK AB (PUBL), Malmö (SE)

( * ) Notice: Subject to any disclaimer, the term of this patent is extended or adjusted under 35 U.S.C. 154(b) by 675 days.

(21) Appl. No.: 17/267,097

(22) PCT Filed: Aug. 20, 2019

(86) PCT No.: PCT/SE2019/050766
§ 371 (c)(1),
(2) Date: Feb. 9, 2021

(87) PCT Pub. No.: WO2020/040687
PCT Pub. Date: Feb. 27, 2020

(65) Prior Publication Data
US 2021/0161167 A1     Jun. 3, 2021

(30) Foreign Application Priority Data
Aug. 24, 2018   (SE) .................................... 1851011-5

(51) Int. Cl.
*C07C 67/52*   (2006.01)
*A23D 9/04*   (2006.01)
(Continued)

(52) U.S. Cl.
CPC .................. *C11B 7/00* (2013.01); *A23D 9/04* (2013.01); *B01D 9/0004* (2013.01); *B01D 9/004* (2013.01);
(Continued)

(58) Field of Classification Search
CPC .... B01D 9/004; B01D 9/0004; B01D 9/0081; C11B 7/00; C07C 67/52
See application file for complete search history.

(56) References Cited

U.S. PATENT DOCUMENTS 6,630,185 B2   10/2003  Arends et al.
9,370,196 B2    6/2016  Sadakane et al.
(Continued)

FOREIGN PATENT DOCUMENTS

CN    102229860 A  * 11/2011  ............... C11B 7/00
CN    102719311 A    10/2012
(Continued)

OTHER PUBLICATIONS

CN102229860 (A), Aijun Hu, et al., Supersonic wave method for promoting rapid crystallization and Fractionation of Palm Oil, English translation, 10 pages (Year: 2011).*
(Continued)

*Primary Examiner* — Yate' K Cutliff
(74) *Attorney, Agent, or Firm* — Finnegan, Henderson, Farabow, Garrett & Dunner, LLP (57) ABSTRACT

A process for dry fractionation of a soft palm oil mid fraction (SPMF) into a final hard palm oil mid fraction (fHPMF-A) is disclosed. The process comprises: providing the solf palm oil mid fraction (SPMF), using the soft palm oil mid fraction (SPMF) as an input (IN1) to a first dry fractionation (FDF) to obtain an intermediate olein fraction (SPMF-O) and an intermediate stearin fraction (SPMF-S), using the intermediate olein fraction (SPMF-O) as an input (IN2) to an ultrasound assisted second dry fractionation (SDF) to obtain the final hard palm oil mid fraction (fHPMF-A) and a palm oil olein fraction (POO), wherein the ultrasound assisted second dry fractionation (SPF) comprises subjecting at least a part of the input (IN2) to ultrasonic treatment (US2). Also disclosed is a final hard palm oil mid fraction (fHPMF-A),
(Continued)

a second hard palm oil mid fraction (sHPMF-B), a hard palm oil mid fraction mixture, and uses of these.

23 Claims, 5 Drawing Sheets (51) Int. Cl.
  *B01D 9/00*   (2006.01)
  *C11B 7/00*   (2006.01)
  *A23G 1/36*   (2006.01)

(52) U.S. Cl.
  CPC ............ *B01D 9/0081* (2013.01); *C07C 67/52* (2013.01); *A23G 1/36* (2013.01); *A23V 2002/00* (2013.01); *B01D 2009/0086* (2013.01)

(56) References Cited

U.S. PATENT DOCUMENTS

| | | | | |
|---|---|---|---|---|
| 2002/0031577 | A1* | 3/2002 | Arends | ................ B01D 9/0081 426/601 |
| 2009/0136619 | A1* | 5/2009 | Uehara | ..................... C11C 3/10 426/33 |
| 2015/0056361 | A1* | 2/2015 | Mizushima | ........... C11B 7/0075 426/660 |

FOREIGN PATENT DOCUMENTS

| | | |
|---|---|---|
| CN | 106566656 A | 4/2017 |
| EP | 2 042 607 A1 | 4/2009 |
| EP | 2 832 226 A1 | 2/2015 |
| JP | 11-169191 | 6/1999 |
| JP | 2002-226886 A | 8/2002 |
| RU | 2 532 044 C1 | 10/2014 |
| RU | 2 654 801 C2 | 5/2018 |
| WO | WO 02/05921 A1 | 1/2002 |
| WO | WO 2015/024791 A1 | 2/2015 |
| WO | WO-2019103667 A1 * | 5/2019 ........... B01D 9/0013 |

OTHER PUBLICATIONS

Gibon, V., Palm Oil and Palm Kernel Oil refining and Fractionation Technology, Palm Oil: Production, processing, characterization and used, AOCS Press US, pp. 329-375 (Year: 2011).*
Chen et al., "Effects of Ultrasonic Parameters on the Crystallization Behavior of Palm Oil," J Am Oil Chem Soc, vol. 90, pp. 941-949 (2013).
Deora et al., "Ultrasound for Improved Crystallisation in Food Processing," Food Eng Rev, vol. 5, pp. 36-44 (2013).
Gibon, "Palm Oil and Palm Kernel Oil Refining and Fractionation Technology," Palm Oil: Production, Processing, Characterization, and Uses, pp. 329-375 (2012).
Hashimoto et al., "Preparation of Sharp-Melting Hard Palm Midfraction and Its Use as Hard Butter in Chocolate," JAOCS, vol. 78, No. 5, pp. 455-460 (2001).
Jin et al., "Characteristics of palm mid-fractions produced from different fractionation paths and their potential usages," International Journal of Food Properties, vol. 21, No. 1, pp. 58-69 (2018).
Kellens et al., "Palm oil fractionation," Eur. J. Lipid Sci. Technol., vol. 109, pp. 336-349 (2007).
Patrick et al., "The effect of ultrasonic intensity on the crystal structure of palm oil," Ultrasonics Sonochemistry, vol. 11, pp. 251-255 (2004).
Ye et al., "Application of High-Intensity Ultrasound to Palm Oil in a Continuous System," J. Agric. Food Chem, vol. 63, pp. 319-327 (2015).
International Search Report for International Application No. PCT/SE2019/050766, mailed Nov. 1, 2019.
Written Opinion of the International Searching Authority for International Application No. PCT/SE2019/050766, mailed Nov. 1, 2019.

* cited by examiner

PROCESS FOR DRY FRACTIONATION TO OBTAIN A FINAL HARD PALM OIL MID FRACTION

FIELD OF INVENTION

The invention relates to a process for dry fractionation to obtain a final hard palm oil mid fraction, particularly using ultrasound assisted dry fractionation.

BACKGROUND

Fractionation of soft palm oil mid fractions into hard palm oil mid fractions is commonly used, typically involving solvent fractionation.

One drawback of solvent fractionations that it is a very costly process, both in terms of operational costs and in terms of construction costs.

When trying to use dry fractionation, drawbacks include problems with obtaining a satisfactory output quality and output yield.

An example of dry fractionation of palm oil olein is described in Hashimoto, S., Nezy, T., Arakawa, H., Ito, T., Maruzeni, S. "Preparation of Sharp-Melting Hard Palm Midfraction and Its Use as Hard Butter in Chocolate", J. Am. Oil. Chem. Soc., Vol. 78, No. 5, 2001, page 455-460. The PMF IV 45 is kept in the crystallization filter for a very long time (48-65 hours) where it is heated to further remove olein. The yields are extremely low and the method is not feasible in production scale. Nowhere does the article mention using ultrasound treatment to overcome the problems with low yield.

JP2014162859 described the general effect of ultrasound on fat and describes how ultrasound can be used to produce very small crystals. In order for dry fractionation to work there has to be crystals of a certain size in order for separation to actually take place. Thus, based on the teaching in this document it would not be obvious to use ultrasound in a dry fraction process.

The generation of very small crystal after subjecting fat to ultrasound is described in several publications. In the article by Yubin Ye et al. ("Using High Intensity Ultrasound as a Tool to Change the Functional Properties of Interesterified Soybean Oil", Journal of Agricultural and Food Chemistry, 2011, 59, page 10712-10722) it is described how high intensity ultrasound can be used to change crystallization behavior and generate small crystals in soybean oil. Fangfang Chen et al. ("Effects of Ultrasonic Parameters on the Crystallization Behavior of Palm Oil", AOCS 2013, 90, page 941-949) describes the same generation of small and uniformly crystals in palm oil after ultrasound treatment.

Thus, based on the prior art it is counter intuitive that ultrasound would work in connection with dry fractionation where small crystals is not desired and instead good separation is needed.

The present invention solves the above problems of low yield and poor quality by combining dry fractionation with ultrasound.

SUMMARY

The present invention relates to a process for dry fractionation of a soft palm oil mid fraction into a final hard palm oil mid fraction, the process comprising:
providing the soft palm oil mid fraction,
using the soft palm oil mid fraction as an input to a first dry fractionation to obtain an intermediate olein fraction and an intermediate stearin fraction,
using the intermediate olein fraction as an input to an ultrasound assisted second dry fractionation to obtain the final hard palm oil mid fraction and a palm oil olein fraction, wherein the ultrasound assisted second dry fractionation comprises subjecting at least a part of the input to ultrasonic treatment.

Advantages of the invention includes obtaining high yields of the final hard palm oil mid fraction having a good quality while realizing a cost-effective process.

According to an embodiment of the invention, the process further comprises using the intermediate stearin fraction as an input to a third dry fractionation to obtain a second hard palm oil mid fraction and a palm oil stearin fraction.

The invention further relates to a final hard palm oil mid fraction,
the final hard palm oil mid fraction comprising POP-triglycerides in an amount of at least 62 percent by weight of the final hard palm oil mid fraction,
the final hard palm oil mid fraction comprising PPP-triglycerides in an amount of less than 2 percent by weight of the final hard palm oil mid fraction,
the final hard palm oil mid fraction having an iodine value (IV) below 38, wherein the final hard palm oil mid fraction has a weight ratio between SatOSat-triglycerides and SatSatO-triglycerides, which is above 15.

The invention further relates to a second hard palm oil mid fraction,
the second hard palm oil mid fraction comprising POP-triglycerides in an amount of at least 64 percent by weight of the second hard palm oil mid fraction,
the second hard palm oil mid fraction comprising PPP-triglycerides in an amount of less than 3 percent by weight of the second hard palm oil mid fraction,
the second hard palm oil mid fraction having an iodine value (IV) below 35, wherein the second hard palm oil mid fraction has a weight ratio between SatOSat-triglycerides and SatSatO-triglycerides, which is below 10.

The invention further relates to a hard palm oil mid fraction mixture comprising
the final hard palm oil mid fraction according to the invention or any of its embodiments or obtained by the process according to the invention or any of its embodiments, and
the second hard palm oil mid fraction according to the invention or any of its embodiments or obtained by the process according to the invention or any of its embodiments,
wherein the hard palm oil mid fraction mixture has a weight ratio between the final hard palm oil mid fraction and the second hard palm oil mid fraction is between 0.4 and 0.6, such as 0.5.

The invention further relates to use of the final hard palm oil mid fraction according to the invention or any of its embodiments or obtained by the process according to the invention or any of its embodiments, the second hard palm oil mid fraction according to the invention or any of its embodiments or obtained by the process according to the invention or any of its embodiments, the hard palm oil mid fraction mixture according to the invention or any of its embodiments, or any mixture thereof in the production of an edible product or a food product.

The invention further relates to use of the final hard palm oil mid fraction according to the invention or any of its embodiments or obtained by the process according to the invention or any of its embodiments, the second hard palm oil mid fraction according to the invention or any of its embodiments or obtained by the process according to the invention or any of its embodiments, the hard palm oil mid fraction mixture according to the invention or any of its embodiments, or any mixture thereof in the production of confectionary products, such as chocolate.

The invention further relates to use of the final hard palm oil mid fraction according to the invention or any of its embodiments or obtained by the process according to the invention or any of its embodiments, the second hard palm oil mid fraction according to the invention or any of its embodiments or obtained by the process according to the invention or any of its embodiments, the hard palm oil mid fraction mixture according to the invention or any of its embodiments, or any mixture thereof in the production of cocoa butter equivalents.

FIGURES

The invention will now be described with reference to the FIGURES where.

DETAILED DESCRIPTION

As used herein, the term "fatty acid" encompasses free fatty acids and fatty acid residues in triglycerides.

As used herein, "%" or "percentage" all relates to weight percentage, i.e. wt. % or wt.-% if nothing else is indicated.

As used herein, the singular forms "a", "an" and "the" include plural referents unless the context clearly dictates otherwise.

As used herein, "at least one" is intended to mean one or more, i.e. 1, 2, 3, 4, 5, 6, 7, 8, 9, 10, etc.

As used herein, the term "triglycerides" may be used interchangeably with the term 'triacylglycerols' and should be understood as an ester derived from glycerol and three fatty acids. "Triglycerides" may be abbreviated TG or TAG. A single triglyceride molecule, having a specific molecular formula, is of either vegetable or non-vegetable origin.

As used herein, the term "cooling" is intended to mean a process of lowering the temperature. This may be done in various ways, but typically includes contacting the composition in question with a cooled surface, e.g. such that one side of the surface is contacted with the composition to be cooled, while the opposite surface is contacted with a coolant. It is noted that while specific cooling steps is included in some embodiments, additional cooling may be included in other steps as well.

As used herein, the term "fraction" is intended to mean a product of a fractionation process. The fractionation product, i.e. the fraction, may or may not be further treated in various other ways. However, it is to be understood that if a certain fraction undergoes a further fractionation, two new, separate fractions are obtained. In other words, when a fraction is subjected to a further fractionation, the original fraction ceases to exist, whereas the two new, separate fractions have replaced it. In some cases, the term "fraction" may be omitted, e.g. the terms "stearin" and "stearin fraction" may be used interchangeably, also the terms "olein" and "olein fraction" may be used interchangeably.

As used herein, the term "supersaturation" is intended to have its ordinary meaning of a supersaturated solution, i.e. intended to mean a solution that contains more of the dissolved material (solute) than could be dissolved by the solvent under normal circumstances. Thus, the "supersaturation threshold" is reached when the composition is supersaturated.

As used herein, the term "dry fractionation" is intended to mean a fractionation without the use of an organic solvent. Organic solvents, such as e.g. acetone and hexane, is used in solvent fractionation to disperse the crystals of the solid fraction in or to flush the liquid part of the oil out. The dry fractionation includes at least melting the input to transform into liquid state any solid parts, cooling and crystallizing the melted input before the final filtering to obtain the resulting fractions.

As used herein, the term "melted" is intended to refer to a completely melted fraction, i.e. a fraction where all triglycerides are completely melted and hence which do not have any content of crystalline triglycerides. The melted composition may be obtained by melting an initial composition, or by obtaining the melted composition from a source of such melted compositions.

As used herein, the term "ultrasonic treatment" is intended to mean a process of treating the input with ultrasound, specifically in the first and second dry fractionation by subjecting the supersaturated soft palm oil mid fraction and intermediate olein fraction, respectively, to ultrasound. The use of ultrasound in the first dry fractionation is optional and included in some embodiments of the invention. In the second dry fractionation and also in the first dry fractionation, if ultrasound treatment is applied, the ultrasound treatment is applied when the input has been processed into supersaturated state. The ultrasound treatment is performed such that at least a part of the crystallization is subsequent to the ultrasound treatment in the respective dry fractionation. The ultrasonic treatment induces crystalline nucleation in the supersaturated palm oil olein in a relatively effective and homogenous way. Throughout the application the terms "ultrasound" and "ultrasonic" may be used interchangeably. Ultrasonic treatment may be done by an ultrasound emitting apparatus. Applicable average ultrasound frequencies include frequencies within the range of 5 to 200 kHz, such as 10 to 100 kHz. High intensity ultrasound is applicable. For example, usable acoustic energies include of at least 50 Joules per Liter of the input, such as between 50 and 10.000 Joules per Liter of the input, such as between 50 and 5.000 Joules per Liter of the input As used herein, the term "ultrasound emitting apparatus" is intended to mean an apparatus capable of emitting ultrasound usable in the ultrasonic treatment of the invention. The ultrasound emitting apparatus may e.g. be an ultrasonic cell, an ultrasonic flowcell, a sonotrode, etc.

As used herein, the term "crystallization" is intended to mean maintaining a supersaturated composition which may or may not, depending on the circumstances, have been fully or partly subjected to ultrasonic treatment. According to embodiments of the invention, the step of crystallization is carried out in the crystallizer, i.e. all of the composition(s) in question is/are crystallized in crystallizer(s). Throughout the application the terms "crystallizing" and "crystallization of" may be used interchangeably.

As used herein the term "hard palm oil mid fraction" is intended to refer to a fraction obtained by fractionations of palm oil, having a content of POP-triglycerides of at least 62% by weight of the hard palm oil mid fraction, having a content of PPP-triglycerides below 4% by weight of the hard palm oil mid fraction, having an iodine value (IV) below 38, and having a weight ratio between SatOSat-triglycerides and SatSatO-triglycerides above 5.

As used herein the term "soft palm oil mid fraction" is intended to refer to a fraction obtained by fractionations of palm oil, having a content of POP-triglycerides between 40 and 55% by weight of the soft palm oil mid fraction, having a content of PPP-triglycerides below 5% by weight of the soft palm oil mid fraction, and having an iodine value (IV) between 50 and 38.

As used herein the term "higher melting fraction" is intended to refer to the fraction with the highest melting point from a given fractionation process. The term "stearin fraction" is used interchangeably therewith.

As used herein the term "lower melting fraction" is intended to refer to the fraction with the lowest melting point from a given fractionation process. The term "olein fraction" is used interchangeably therewith.

As used herein the term "intermediate olein fraction" is intended to refer to the lower melting fraction of the first dry fractionation, i.e. the fraction with the lowest melting point. Since the first dry fractionation is followed by a subsequent, second dry fractionation, and the fractionation products of the first dry fractionation thus are not the final products, these are referred to as intermediate fractionation products.

As used herein the term "intermediate stearin fraction" is intended to refer to the higher melting fraction of the first dry fractionation, i.e. the fraction with the highest melting point. Since the first dry fractionation is followed by a subsequent, second dry fractionation, and the fractionation products of the first dry fractionation thus are not the final products, these are referred to as intermediate fractionation products.

As used herein, the term "slurry" is intended to mean a composition comprising both crystalline components and also liquid components thus together having a slurry like state. In other words, the term "slurry" is a partly melted composition where at least some crystals are present. Thus, a "slurry" may also be understood as a partly melted suspension, partly molten suspension or a paste.

As used herein, the term "de-topping" is intended to mean any process of removing PPP-triglycerides. It may typically be a de-topping fractionation, which is a process of fractionating at an elevated temperature of the palm oil mid fraction, such as around 25 to 30 degrees Celsius with the purpose of removing PPP-triglycerides. The elevated temperature at which the fractionation de-topping is performed is due to the relatively high melting point of PPP-triglycerides.

As used herein, the term "iodine value" is intended to mean an iodine value obtained according to IUPAC 2.205/4-7th edition, unless otherwise specified. The iodine value may also be referred to as "Wijs iodine value", "Wijs IV", or simply "IV".

As used herein, the term "crystallizer" is intended to mean a vessel for performing crystallization. The crystallizer may be a dynamic crystallizer, i.e. a crystallizer with agitation, or static crystallizer without any agitation. Crystallizers are often provided with a cooling arrangement, e.g. in the form of a water jacket, but this is not necessary in all embodiments. Examples of usable crystallizers include dynamic crystallizers, such as DeSmet Ballestra L-Frac units or Tirtiux, DeSmet Ballestra Mobulizer, and static crystallizers, such as a DeSmet Ballestra Statoliser.

As used herein, the term "cocoa butter equivalent" is intended to mean an edible fat having very similar physical properties and being compatible with cocoa butter without any significant effect on the behavior of the chocolate. In both cocoa butter and cocoa butter equivalent the fatty acids are typically palmitic, stearic and oleic acids and the triglycerides are typically 2-oleo di-saturated (SatOSat). In spite of their similarity to cocoa butter, cocoa butter equivalents can be detected in chocolate by their triglyceride ratios which are appreciably different from those in cocoa butter.

Cocoa butter equivalents are e.g. made from a mix of palm mid fraction and a fractionated part of shea stearin.

ABBREVIATIONS

P=palmitic acid/palmitate
O=oleic acid/oleate
St=stearic acid/stearate
Li=linoleic acid/linoleate
POP-triglyceride=1,3-dipalmitate-2-oleate glycerol
POO-triglyceride=1-palmitate-2,3-dioleate glycerol
OOO-triglyceride=1,2,3-trioleate glycerol
PPP-triglyceride=1,2,3-triplamitate glycerol
SatOSat-triglyceride=1,3-disaturated-2-oleate glycerol
SatSatO-triglyceride=1,2-disaturated-3-oleate glycerol
SatSatSat-triglyceride=1,2,3-trisaturated glycerol
SatUU-triglyceride=1-saturated-2,3-diunsaturated glycerol
UUU-triglyceride=1,2,3-triunsaturated glycerol
XYZ-triglyceride=1-X-2-Y-3-Z glycerol of the fatty acids X, Y, and Z
IV=iodine value The invention relates to a process for dry fractionation of a soft palm oil mid fraction (SPMF) into a final hard palm oil mid fraction (fHPMF-A), the process comprising:
  providing the soft palm oil mid fraction (SPMF),
  using the soft palm oil mid fraction (SPMF) as an input (IN1) to a first dry fractionation (FDF) to obtain an intermediate olein fraction (SPMF-O) and an intermediate stearin fraction (SPMF-S),
  using the intermediate olein fraction (SPMF-O) as an input (IN2) to an ultrasound assisted second dry fractionation (SDF) to obtain the final hard palm oil mid fraction (fHPMF-A) and a palm oil olein fraction (POO),
  wherein the ultrasound assisted second dry fractionation (SDF) comprises subjecting at least a part of the input (IN2) to ultrasonic treatment (US2).

One advantage of the invention is that a surprisingly high yield of the final hard palm oil mid fraction (fHPMF-A) is obtained. Especially, when comparing the yield of the final hard palm oil mid fraction (fHPMF-A) to the yield of corresponding conventional dry fractionations, i.e. without utilization of ultrasound. In this respect, it is emphasized that the high yield is to be considered as a high yield of hard palm oil mid fraction from the soft palm oil mid fraction comparing to conventional processes, where no hard palm oil mid fraction is obtained from the intermediate olein fraction.

Moreover, a further advantage of the invention is that an increased quality of the obtained final hard palm oil mid fraction (fHPMF-A) is achieved, comparing to conventional fractionation of the intermediate olein fraction. This surprisingly high quality is generally characterized by an efficient separation of lower melting point triglycerides from higher melting point triglycerides, and in the present context that the final hard palm mid fraction (fHPMF-A) includes a high content of POP-triglycerides.

Furthermore, the above described high yield is advantageously obtained while at the same time also obtaining a high quality of the final hard palm oil mid fraction (fHPMF-A), comparing to conventional fractionation of the intermediate olein fraction. Conventionally, high yield and high quality is often viewed as two parameters, where the process is adjusted to a desirable tradeoff between yield and quality. Thus, having e.g. a high yield would typically come at the cost of a lower quality, and vice versa. Nevertheless, the present invention surprisingly establishes a process where ultrasonic assisted fractionation is used to obtain a high yield of a high quality final hard palm oil mid fraction (fHPMF-A).

The above advantages are obtained with use of ultrasound assisted dry fractionation, i.e. without the use of solvent fractionation. Solvent fractionation may often be considerably costlier and may also produce a lower quality product from a labelling perspective. Especially, the present invention provides for obtaining the final hard palm oil mid fraction (fHPMF-A) using dry fractionation, i.e. without solvent fractionation, thereby providing for significantly lower construction costs for fractionation plants, since solvent fractionation plants have very high construction costs, and since existing dry fractionation plants may be retrofitted to operate in accordance with the invention in a relatively simple and thus low-cost manner.

Even further, the process of the invention may be performed within a surprisingly short time period, particularly reducing the time of crystallization. This can even be done while attaining the above described high yield and high quality.

Thus, a significant increase in the fractionation capacity for a given fractionation plant may be obtained. This may be in part due to the shortened fractionation time. However, it may also in part due to the increased quality, whereby extra fractionation steps are avoided.

Due to the above advantages, particularly including high yield and quality and also the increase in fractionation quality, a notable increase in cost-effectiveness of the overall process is obtained.

A further advantage of the invention is that conventional fractionation plants may be retrofitted with systems for applying the ultrasound treatment, i.e. the advantages can be obtained without the need for building new fractionation plants.

Moreover, the present inventor surprisingly found that the invention provides a process giving a remarkable consistent output, even when varying the soft palm oil mid fraction used as the first input. This is a significant advantage since it allows a consistent product may be obtained simply as the output of the process of the invention without e.g. adding further fractions or performing further processing, thereby increasing the value of the output relative to the input, and providing advantageous flexibility with respect to the input and thereby with respect to suppliers, different regions etc.

Also, it is noted that the obtained final hard palm oil mid fraction (fHPMF-A) is advantageous in the sense that it has a surprisingly high ratio between SatOSat-triglycerides (i.e. triglycerides with a saturated fatty acid in positions 1 and 3, and a monounsaturated fatty acid in position 2) and SatSatO-triglycerides (i.e. triglycerides with a saturated fatty acid in positions 1 and 2, and a monounsaturated fatty acid in position 3), also referred to as a high symmetry ratio. Having a high symmetry ratio is advantageous when blending with other fats having a high symmetry ratio, e.g. cocoa butter. The symmetry ratio can be obtained from high-performance liquid chromatography (HPLC) measurements of the weight percent content of triglycerides. Such methods are well-known for the skilled person. The skilled person will know how to measure positional isomers of triglycerides just like commercial analysis laboratories can perform the analysis.

A further advantage of the invention is that the obtained final hard palm oil mid fraction (fHPMF-A) may have an advantageous composition, specifically in that it has a low content of asymmetric SatSatO-triglycerides and a corresponding high ratio between SatOSat-triglycerides and SatSatO-triglycerides.

A still further advantage of the invention is that the process provides for a relatively well-defined output, particularly well-defined in terms of the obtained hard palm oil mid fraction. This can be seen from the small standard deviations on the composition of the output (as demonstrated in the examples). In fact, even with different soft palm oil mid fractions as inputs for the process of the invention the resulting quality and composition of the output is remarkably similar.

Thus, in the present context, the input to the first and second dry fractionation is the soft palm oil mid fraction and intermediate olein fraction, respectively. In one embodiment of the invention, the soft palm oil mid fraction is subjected to cooling to provide a supersaturated soft palm oil mid fraction, after initially melting the soft palm oil mid fraction. Similarly, the intermediate olein fraction is subjected to cooling to provide a supersaturated intermediate olein fraction, after melting the intermediate olein fraction. Therefore, when referring to the "input" of the first or second dry fractionations, the soft palm oil mid fraction or intermediate olein fraction, respectively, is meant, that said "input" have been subjected to treatments such as melting, cooling, crystallization etc. during the dry fractionations.

The first dry fractionation may be performed in a number of different ways. In some embodiments, it may comprise ultrasonic treatment, whereas other embodiments are without ultrasonic treatment.

Thus, according to an embodiment of the invention, said first dry fractionation (FDF) is an ultrasound assisted first dry fractionation, comprising subjecting at least part of the input (IN1) to ultrasonic treatment (US2).

An advantage of this is that an even further increase in yield and output quality is made possible.

Alternatively, the first dry fractionation (FDF) is a conventional dry fractionation in the sense that it does not comprise any ultrasonic treatment.

In order to obtain the advantageous output in terms of yield and quality of the desired fractions, it is beneficial to use cooling to a supersaturated stated of the input of the second dry fractionation (SDF) before utilizing ultrasonic treatment (US2).

According to an embodiment of the invention, the ultrasound assisted second dry fractionation (SDF) comprises cooling (CO2) the input (IN2) to obtain a supersaturated input (IN2), prior to the ultrasonic treatment (US2).

In embodiments of the invention, the first and/or second dry fractionation comprise further cooling of the input (IN1, IN2) even after obtaining supersaturated state.

In a further embodiment the second dry fractionation (SDF) comprises crystallization (CRY2) of the supersaturated input (IN2), at least a part of which having been subjected to ultrasound treatment (US2).

In one embodiment the crystallization (CRY2) is performed in a crystallizer, and where the ultrasonic treatment (US2) is performed external to the crystallizer.

Advantages of this includes that a more flexible setup is be achieved in the sense that the crystallization and the ultrasonic treatment is more independent from each other.

In an embodiment of the invention the first and the second crystallizations is performed in the same crystallizer.

In a further embodiment the crystallization (CRY2) is performed in a crystallizer, and where the ultrasonic treatment (US2) is performed in the crystallizer.

Advantages of this include that handling of the input (IN2) from the crystallizer to the ultrasonic treatment and back may be avoided due to the integrated ultrasonic treatment (US2).

According to a further embodiment of the invention, the crystallization (CRY2) is performed in a crystallizer, and where the cooling (CO2) is performed in the crystallizer.

According to an even further embodiment of the invention, the crystallization (CRY2) is performed in a crystallizer, and where the cooling (CO2) is performed external to the crystallizer.

According to a still further embodiment of the invention, the crystallization (CRY2) is performed in a crystallizer, and where the cooling (CO2) is performed both internal in the crystallizer and external to the crystallizer.

It is noted that the use of "second" in the above embodiments, e.g. as the second melting (step), the second cooling (step), the second crystallization (step), the second filtration (step), and the second slurry, denotes the association with the second dry fractionation. Thus, "second" is used only to distinguish it from any corresponding "first" step, whether such step is present in the process or not.

As previously mentioned, the first dry fractionation (FDF) comprises ultrasound treatment (US1) in some embodiments.

In a still further embodiment the first dry fractionation (FDF) comprises a crystallization (CRY1) of the supersaturated input (IN1), at least a part of which having been subjected to ultrasound treatment (US1).

In an embodiment, the first dry fractionation (FDF) comprises an ultrasonic treatment (US1), and the first dry fractionation (FDF) comprises cooling (CO1) the input (IN1) to obtain a supersaturated input (IN1), prior to the ultrasonic treatment (US1).

In a further embodiment the crystallization (CRY1) of the first dry fractionation (FDF) is performed in a crystallizer, and where the ultrasonic treatment (US1) of the first dry fractionation (FDF) is performed external to the crystallizer.

In an even further embodiment the crystallization (CRY1) of the first dry fractionation (FDF) is performed in a crystallizer, and where the ultrasonic treatment (US1) of the first dry fractionation (FDF) is performed in the crystallizer.

According to a still further embodiment of the invention, the crystallization (CRY1) of the first dry fractionation (FDF) is performed in a crystallizer, and where the cooling (CO1) of the first dry fractionation (FDF) is performed in the crystallizer.

According to a still even further embodiment of the invention, the crystallization (CRY1) of the first dry fractionation (FDF) is performed in a crystallizer, and where the cooling (CO1) of the first dry fractionation (FDF) is performed external to the crystallizer.

According to an even further embodiment of the invention, the crystallization (CRY1) of the first dry fractionation (FDF) is performed in a crystallizer, and where the cooling (CO1) of the first dry fractionation (FDF) is performed in the crystallizer and external to the crystallizer.

According to an embodiment of the invention, the first dry fractionation (FDF) comprises
- melting, in a first melting step (MLT1), the soft palm oil mid fraction (SPMF) to obtain a melted soft palm oil mid fraction (mSPMF),
- cooling, in a first cooling step (CO1), the melted palm oil mid fraction (SPMF) to obtain a supersaturated soft palm oil mid fraction (ssSPMF),
- crystallization, in a first crystallization step (CRY1), of the supersaturated soft palm oil mid fraction (ssSPMF) to obtain a first slurry (SL1), and
- filtering, in a first filtration step (FLT1), the first slurry (SL1) to obtain the intermediate olein fraction (SPMF-O) and the intermediate stearin fraction (SPMF-S).

It is noted that the use of "first" in the above embodiments, e.g. as the first melting step, the first cooling step, the first crystallization step, the first filtration step, and the first slurry, denotes the association with the first dry fractionation. Thus, "first" is used only to distinguish it from any corresponding "second" step, whether such step is present in the process or not.

According to a further embodiment, the first dry fractionation (FDF) further comprises the step of
- subjecting, in an ultrasonic treatment (US1), at least a part of the supersaturated soft palm oil mid fraction (ssSPMF) to ultrasound.

According to an embodiment of the invention, the second dry fractionation (SDF) comprises
- melting, in a second melting step (MLT2), the intermediate olein fraction (SPMF-O) to obtain a melted intermediate olein fraction (mSPMF-O),
- cooling, in a second cooling step (CO2), the melted intermediate olein fraction (mSPMF-O) to obtain a supersaturated intermediate olein fraction (ssSPMF-O),
- subjecting, in an ultrasonic treatment (US2), at least a part of the supersaturated intermediate olein fraction (ssSPMF-O) to ultrasound,
- crystallization, in a second crystallization step (CRY2), of the supersaturated intermediate olein fraction (ssSPMF-O) having at least partly been subjected to ultrasonic treatment (US2) to obtain a second slurry (SL2),
- filtering, in a second filtration step (FLT2), the second slurry (SL2) to obtain the final hard palm oil mid fraction (fHPMF-A) and the palm oil olein fraction (POO).

It is noted that the use of "second" in the above embodiment, e.g. as the second melting step, the second cooling step, the second crystallization step, the second filtration step, and the second slurry, denotes the association with the second dry fractionation. Thus, "second" is used only to distinguish it from any corresponding "first" step, whether such step is present in the process or not.

According to a further embodiment of the invention, the palm oil olein fraction (POO) is used for obtaining a further soft palm oil mid fraction (SPMF).

According to a still further embodiment of the invention, the process comprises a further preceding dry fractionation (PDF) of the palm oil olein (POO) to obtain a soft palm oil mid fraction (SPMF) and a super olein fraction (SOF).

Advantageously, the further preceding dry fractioning may be an ultrasound assisted preceding dry fractionation comprising ultrasonic treatment of at least a part of the palm oil olein to obtain a soft palm oil mid fraction and a super olein fraction.

According to an embodiment of the invention, the first melting step and the second melting step are performed by the same melting apparatus.

According to a further embodiment of the invention, the first cooling step and the second cooling step are performed by the same cooling apparatus.

According to a still further embodiment of the invention, the ultrasonic treatments (US1, US2) of the first and second dry fractionations (FDF, SDF) are performed by the same ultrasound apparatus.

According to an even further embodiment of the invention, the first crystallization step and the second crystallization step are performed by the same crystallization apparatus.

According to a still even further embodiment of the invention, the first filtration step and the second filtration step are performed by the same filtering apparatus.

According to an embodiment of the invention, the first dry fractionation (FDF) and the second dry fractionation (SDF) is performed using the same dry fractionation system.

According to a further embodiment of the invention, the step of cooling the palm oil olein (POO) is performed in said crystallizer CRS, wherein at least part of the supersaturated palm oil olein ssPO is fed from the crystallizer CRS to an ultrasound emitting apparatus arranged external to said crystallizer CRS, and wherein the palm oil olein having been subjected to ultrasonic treatment in said ultrasound emitting apparatus is fed back into said crystallizer CRS.

According to an embodiment of the invention, the ultrasonic treatment (US2) has a duration of at least 5 minutes.

According to a further embodiment of the invention, the ultrasound treatment has a duration of between 5 minutes and 180 minutes.

According to a still further embodiment of the invention, the ultrasound treatment has a duration of between 10 minutes and 180 minutes.

According to an embodiment of the invention, the ultrasound treatment (US2) is performed on at least 5% by weight of the intermediate olein fraction (SPMF-O).

According to an embodiment of the invention, the ultrasound treatment (US2) is performed at an average frequency of ultrasound of between 5 and 200 kHz, such as between 10 and 100 kHz.

According to an embodiment of the invention, the ultrasound treatment (US2) is performed having an acoustic energy of at least 50 Joules per Liter of the input (IN2), such as between 50 and 10.000 Joules per Liter of the input (IN2), such as between 50 and 5.000 Joules per Liter of the input (IN2).

According to an embodiment of the invention, the cooling (CO2) has a duration of at least 2 hours after reaching a supersaturation threshold, such as between 2 and 30 hours after reaching a supersaturation threshold.

According to an embodiment of the invention, the cooling has a duration of at least 4 hours after reaching a supersaturation threshold, such as between 4 and 30 hours after reaching a supersaturation threshold.

According to an embodiment of the invention, the final hard palm oil mid fraction (fHPMF-A) is obtained in an amount of 15 to 50% by weight of the soft palm oil mid fraction (SPMF).

According to an embodiment of the invention the final hard palm oil mid fraction (fHPMF-A) is obtained in an amount of 20 to 40% by weight of the soft palm oil mid fraction (SPMF).

According to an embodiment of the invention, the process further comprises
using the intermediate stearin fraction (SPMF-S) as an input (IN3) to a third dry fractionation (TDF) obtain a second hard palm oil mid fraction (sHPMF-B) and a palm oil stearin fraction (POSt).

Thus, this embodiment highly advantageously provides a second hard palm oil mid fraction (sHPMF-B), a separate and additional fraction to the final hard palm oil mid fraction (fHPMF-A) of the invention. Thereby, a very efficient utilization of the soft palm oil mid fraction (SPMF) for the production of hard palm oil mid fractions (fHPMF-A, sHPMF-B) is obtained.

Moreover, the obtained second hard palm oil mid fraction (sHPMF-B) obtained from the third dry fractionation (TDF) has an increased content of asymmetric triglycerides, specifically an increased ratio between asymmetric SatSatO-triglycerides and SatOSat-triglycerides. This for example provides bloom inhibition when using the second hard palm oil mid fraction (sHPMF-B) in chocolate production, e.g. as a part of a cocoa butter equivalent.

According to an embodiment of the invention, the third dry fractionation (TDF) comprises
melting, in a third melting step (MLT3), the intermediate stearin fraction (SPMF-S) to obtain a melted intermediate stearin fraction (mSPMF-S),
cooling, in a third cooling step (CO3), the melted intermediate stearin fraction (mSPMF-S) to obtain a supersaturated intermediate stearin fraction (ssSPMF-S),
crystallization, in a third crystallization step (CRY3), of the supersaturated intermediate stearin fraction (ssSPMF-S) to obtain a third slurry (SL3), filtering the third slurry (SL3) to obtain the second hard palm oil mid fraction (sHPMF-B) and the palm oil stearin fraction (POSt).

The invention further relates to a final hard palm oil mid fraction (fHPMF-A),
the final hard palm oil mid fraction (fHPMF-A) comprising POP-triglycerides in an amount of at least 62 percent by weight of the final hard palm oil mid fraction (fHPMF-A),
the final hard palm oil mid fraction (fHPMF-A) comprising PPP-triglycerides in an amount of less than 2 percent by weight of the final hard palm oil mid fraction (fHPMF-A),
the final hard palm oil mid fraction (fHPMF-A) having an iodine value (IV) below 38, wherein the final hard palm oil mid fraction (fHPMF-A) has a weight ratio between SatOSat-triglycerides and SatSatO-triglycerides, which is above 15.

According to an embodiment of the invention, the final hard palm oil mid fraction (fHPMF-A) is obtained by the process according to the invention or any of its embodiments.

An advantage of the invention is that the obtained final hard palm oil mid fraction (fHPMF-A) has an advantageous composition, specifically in that it has a high ratio between SatOSat-triglycerides and SatSatO-triglycerides reflective a relatively low content of asymmetric SatSatO-triglycerides.

The invention further relates to a second hard palm oil mid fraction (sHPMF-B),
the second hard palm oil mid fraction (sHPMF-B) comprising POP-triglycerides in an amount of at least 64 percent by weight of the second hard palm oil mid fraction (sHPMF-B),
the second hard palm oil mid fraction (sHPMF-B) comprising PPP-triglycerides in an amount of less than 3 percent by weight of the second hard palm oil mid fraction (sHPMF-B), the second hard palm oil mid fraction (sHPMF-B) having an iodine value (IV) below 35,
wherein the second hard palm oil mid fraction (sHPMF-B) has a weight ratio between SatOSat-triglycerides and SatSatO-triglycerides, which is below 10.

Advantageously, the second hard palm oil mid fraction (sHPMF-B) obtained from the third dry fractionation (TDF) has an increased content of asymmetric triglycerides, specifically an increased ratio between asymmetric SatSatO-triglycerides and SatOSat-triglycerides. This for example provides bloom inhibition when using the second hard palm oil mid fraction (sHPMF-B) in chocolate production, e.g. as a part of a cocoa butter equivalent.

According to an embodiment of the invention, the second hard palm oil mid fraction (sHPMF-B) is obtained by the process according to the invention or any of its embodiments.

The invention further relates to a hard palm oil mid fraction mixture comprising
the final hard palm oil mid fraction (fHPMF-A) of the invention or any of its embodiments or obtained by the process of the invention or any of its embodiments, and
the second hard palm oil mid fraction (sHPMF-B) of the invention or any of its embodiments or obtained by the process of the invention or any of its embodiments, wherein the hard palm oil mid fraction mixture has a weight ratio between the final hard palm oil mid fraction (fHPMF-A) and the second hard palm oil mid fraction (sHPMF-B) is between 0.4 and 0.6, such as 0.5.

An advantage of this embodiment is that the obtained hard palm oil mid fraction mixture may have a composition highly similar to that of a conventional hard palm oil mid fraction, and that the hard palm oil mid fraction mixture therefore may be produced in increased amounts due to a very effective utilization of the soft palm oil mid fraction for obtaining both the final hard palm oil mid fraction (fHPMF-A) and the second hard palm oil mid fraction (sHPMF-B).

The invention further relates to use of the final hard palm oil mid fraction (fHPMF-A) of the invention or any of its embodiments or obtained by the process of the invention or any of its embodiments, the second hard palm oil mid fraction (sHPMF-B) of the invention or any of its embodiments or obtained by the process of the invention or any of its embodiments, the hard palm oil mid fraction mixture of the invention or any of its embodiments, or any mixture thereof in the production of an edible product or a food product.

The invention further relates to use of the final hard palm oil mid fraction (fHPMF-A) of the invention or any of its embodiments or obtained by the process of the invention or any of its embodiments, the second hard palm oil mid fraction (sHPMF-B) of the invention or any of its embodiments or obtained by the process of the invention or any of its embodiments, the hard palm oil mid fraction mixture of the invention or any of its embodiments, or any mixture thereof in the production of confectionary products, such as chocolate.

The invention further relates to use of the final hard palm oil mid fraction (fHPMF-A) of the invention or any of its embodiments or obtained by the process of the invention or any of its embodiments, the second hard palm oil mid fraction (sHPMF-B) of the invention or any of its embodiments or obtained by the process of the invention or any of its embodiments, the hard palm oil mid fraction mixture of the invention or any of its embodiments, or any mixture thereof in the production of cocoa butter equivalents.

Figure 1:
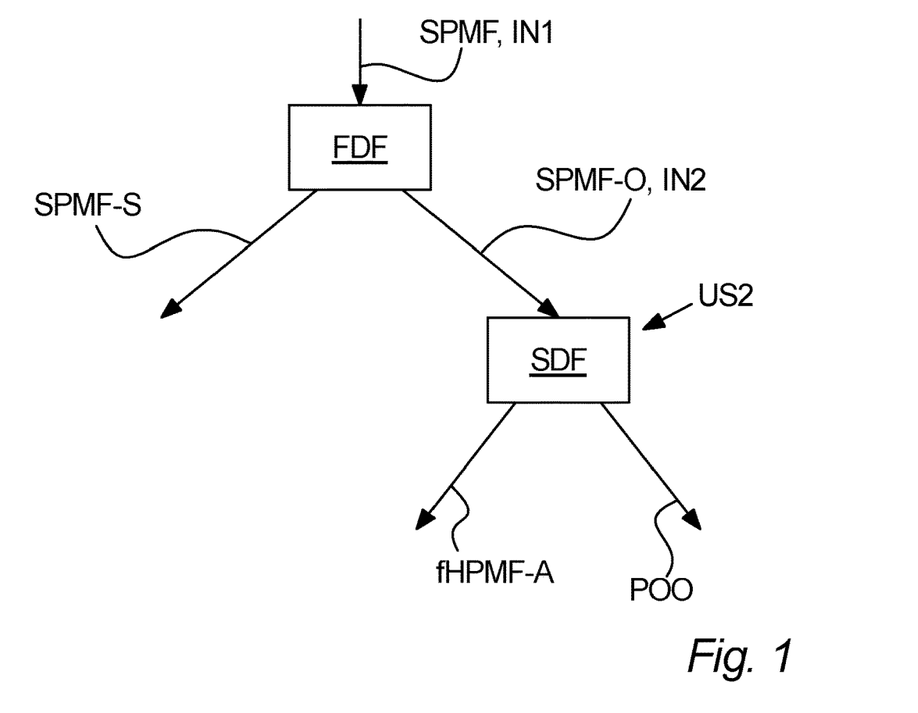
FIG. 1 illustrates a process for dry fractionation of a soft palm oil mid fraction SPMF for obtaining a final hard palm oil mid fraction (fHPMF-A) according to an embodiment of the invention.

Referring to FIG. 1, a process for dry fractionation of a soft palm oil mid fraction (SPMF) into a final hard palm oil mid fraction (fHPMF-A) according to an embodiment of the invention is disclosed. First, the soft palm oil mid fraction (SPMF) is provided.

Figure 3:
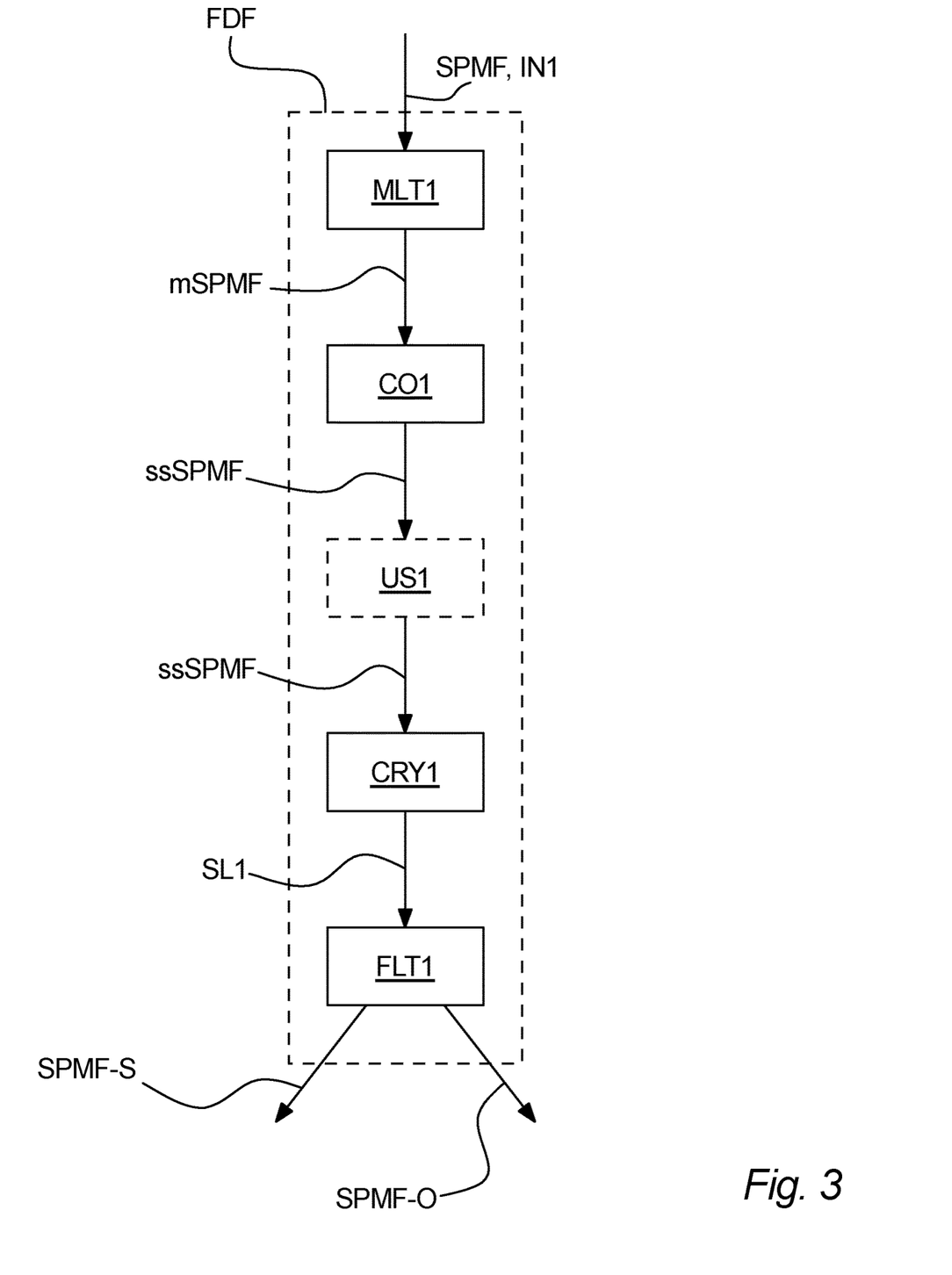
FIG. 3 illustrates the first dry fractionation (FDF) in details according to an embodiment of the invention.

This soft palm oil mid fraction (SPMF) is then used as an input (IN1) to a first dry fractionation (FDF). An intermediate olein fraction (SPMF-O) and an intermediate stearin fraction (SPMF-S) are obtained as output from the first dry fractionation (FDF). The first dry fractionation (FDF) according to one embodiment is illustrated in FIG. 3.

Next, the intermediate olein fraction (SPMF-O) is used as an input (IN2) to an ultrasound assisted second dry fractionation (SDF). The final hard palm oil mid fraction (fHPMF-A) and a palm oil olein fraction (POO) is obtained as output from the second dry fractionation (SDF).

The second dry fractionation (SDF) comprises subjecting at least a part of the input (IN2) to ultrasonic treatment (US2).

Figure 4:
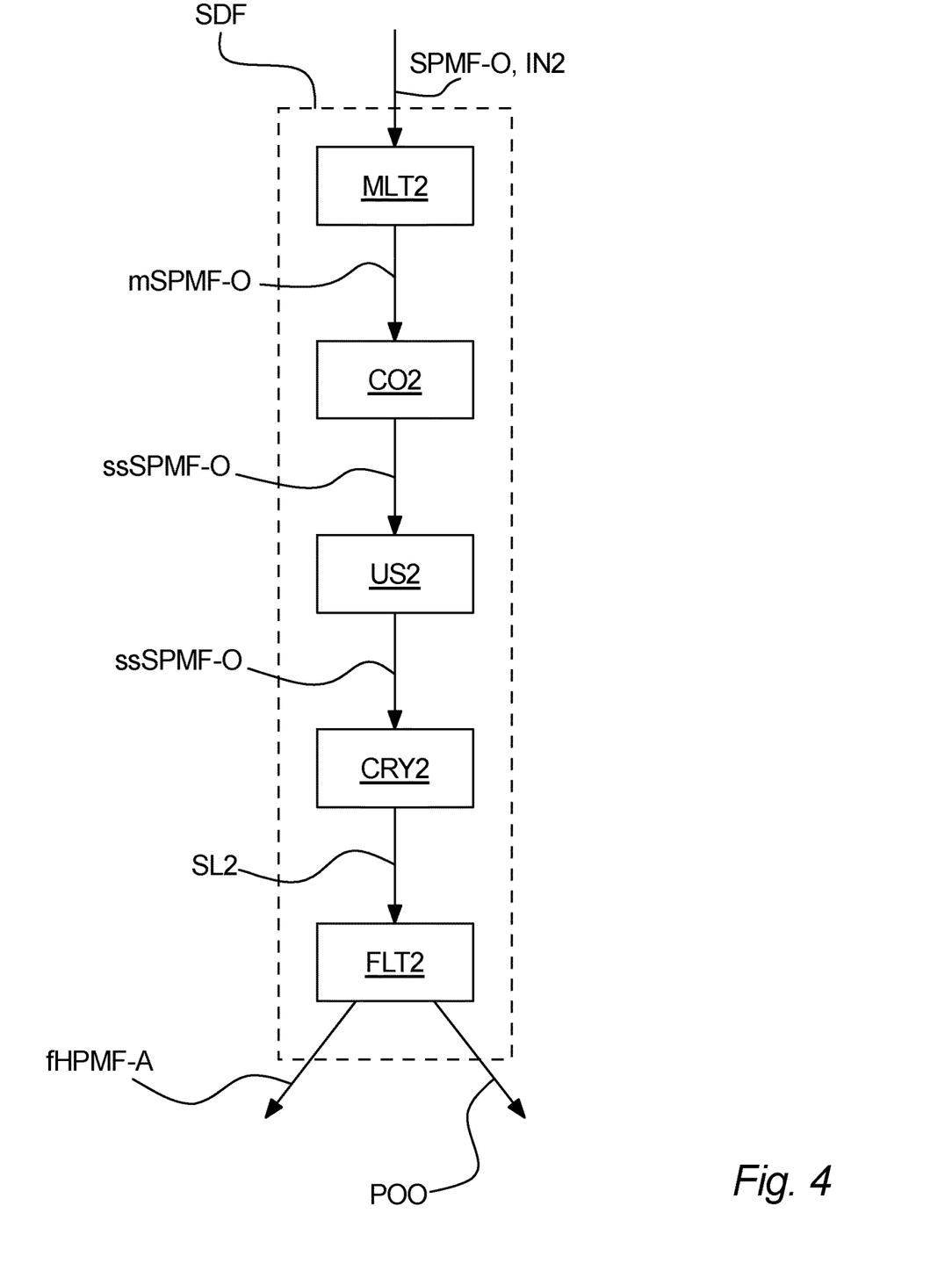
FIG. 4 illustrates the second dry fractionation (SDF) in details according to an embodiment of the invention.

The second dry fractionation (SDF) according to one embodiment is illustrated in FIG. 4.

Different methods may be used to subject at least a part of the input (IN2) to ultrasonic treatment (US2). Examples of an ultrasound emitting apparatus usable within the scope of the invention include e.g. an ultrasonic cell, an ultrasonic flowcell, a sonotrode, etc. The skilled person will know which ultrasound emitting apparatus to use in a given embodiment of the invention.

In some embodiments, the first dry fractionation (FDF) may also comprise subjecting at least a part of the input (IN1) to ultrasonic treatment (US1). However, in other embodiments, the first dry fractionation (FDF) is a conventional dry fractionation, without use of any ultrasonic treatment of the input (IN1).

Figure 2:
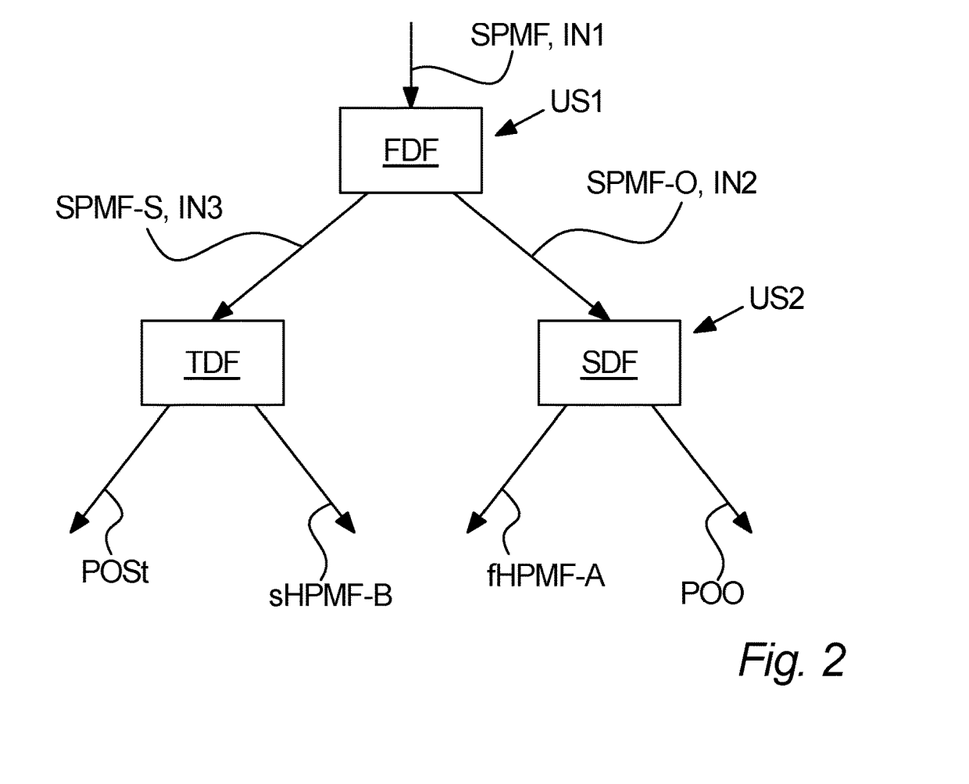
FIG. 2 illustrates a process for dry fractionation of a soft palm oil mid fraction SPMF for obtaining a final hard palm oil mid fraction (fHPMF-A) and a second hard palm oil mid fraction (sHPMF-B) according to an embodiment of the invention.

Referring to FIG. 2, a process for dry fractionation of a soft palm oil mid fraction (SPMF) into a final hard palm oil mid fraction (fHPMF-A) according to a further embodiment of the invention is shown.

The process of FIG. 2 includes, further to the steps of the embodiment of FIG. 1, a third dry fractionation (TDF), where the intermediate stearin fraction (SPMF-S) is fractionated into a palm oil stearin fraction (POSt) and a second hard palm oil mid fraction sHPMF.

Also, FIG. 2 shows the use of ultrasound treatment (US1) in the first dry fractionation (FDF). As e.g. illustrated in FIG. 3, the first dry fractionation may or may not involve ultrasound treatment (US1), depending on the specific embodiment.

Referring to FIG. 3, the first dry fractionation (FDF) is illustrated in more detail according to an embodiment of the invention. In this embodiment, the first dry fractionation comprises a first melting step (MLT1), a subsequent first cooling step (CO1), then a first crystallization step (CRY1), and finally a first filtering step (FLT1).

In the first melting step (MLT1), the soft palm oil mid fraction (SPMF) used as the input (IN1) to the first dry fractionation (FDF) is melted thus ensuring that the resulting melted soft palm oil mid fraction (mSPMF) contains no residual crystalline triglycerides at later stages. Typically, the soft palm oil mid fraction (SPMF) is kept at an elevated temperature for a predetermined duration to ensure complete melting thereof.

In the first cooling step (CO1), the melted soft palm oil mid fraction (mSPMF) is cooled to below the supersaturation threshold, whereby a supersaturated soft palm oil mid fraction (ssSPMF) is obtained.

Then, in the first crystallization step (CRY1), the supersaturated soft palm oil mid fraction (ssSPMF) is crystalized to obtain a first slurry (SL1).

With respect to crystallization, it is noted that crystals may be formed during the crystallization step, but may also be formed during other steps, such as the cooling step and the ultrasound treatment. The crystallization step (CRY1) signifies that the supersaturated soft palm oil mid fraction (ssSPMF) is actively processed to obtain the first slurry (SL1). This processing is known as crystallization, a process that is known for the skilled person.

Finally, in the first filtering step (FLT1), the first slurry (SL1) is filtered to obtain the intermediate olein fraction (SPMF-O) and the intermediate stearin fraction (SPMF-S).

The intermediate olein fraction (SPMF-O) is then subjected to the second dry fractionation (SDF), which is illustrates in FIG. 4.

Returning to FIG. 3, in some embodiments, at least a part of the supersaturated soft palm oil mid fraction (ssSPMF) is subjected to a first ultrasound treatment (US1). As the first ultrasound treatment (US1) is included in some embodiments, but not in other embodiments, and therefore is optional, it is illustrated with dashed lines in FIG. 3. Other steps may also deviate from the illustrations of FIG. 3, however they overall represent a typical way of performing the first dry fractionation, which is essential.

In some embodiments, the intermediate stearin fraction (SPMF-S) is subjected to a third dry fractionation (TDF) to obtain a second hard palm oil mid fraction sHPMF. This is illustrated in FIG. 2.

Typically, the third dry fractionation (TDF) may be a de-topping fractionation for removing especially PPP-triglycerides. An amount of other triglycerides, such as POP-triglycerides may also be removed together with the PPP-triglycerides.

Figure 5:
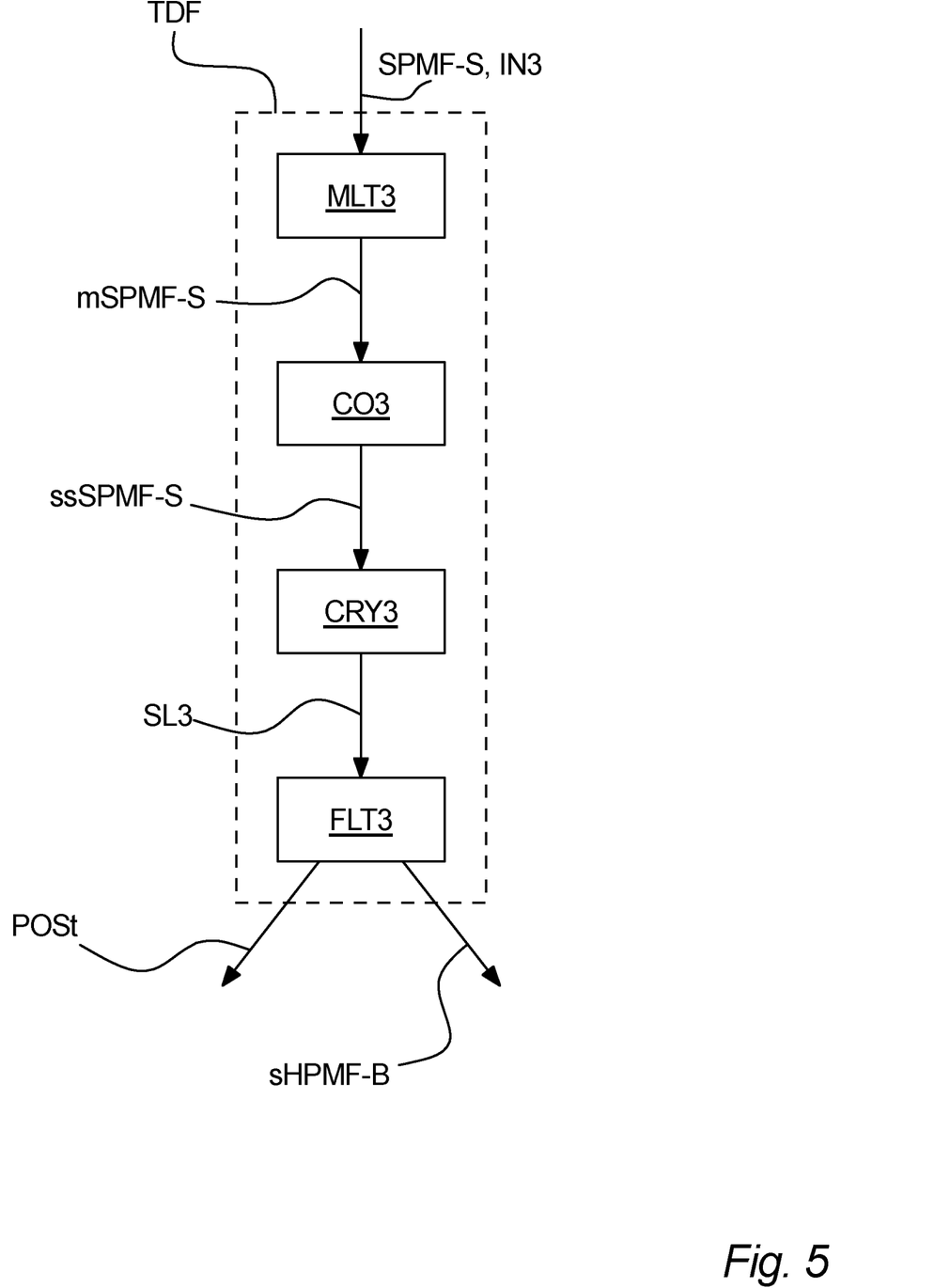
FIG. 5 illustrates the third dry fractionation (TDF) in details according to an embodiment of the invention.

The third dry fractionation (TDF) is illustrated in more detail in FIG. 5 according to an embodiment of the invention. In this embodiment, the intermediate stearin fraction (SPMF-S) is used as an input (IN3) and subjected to a third melting step (MLT3). The obtained melted intermediate stearin fraction (mSPMF-S) is then subjected to a cooling step (CO3), whereby a supersaturated intermediate stearin fraction (ssSPMF-S) is obtained. This supersaturated intermediate stearin fraction (ssSPMF-S) is crystallized in a crystallization step (CRY3) to obtain a third slurry (SL3), which is filtered (FLT3) to obtain the second hard palm oil mid fraction (sHPMF-B) and the palm oil stearin fraction (POSt).

It is noted that while the above described FIGURES represent typical ways of performing the dry fractionation, these are not limiting for the scope of the invention, and the skilled person will appreciate that variations in methods exist.

EXAMPLES

Example 1—Manufacturing of Hard Palm Oil Mid Fractions

First, a soft palm oil mid fraction is heated to 60 degrees Celsius whereby it is completely melted and kept at this temperature for two hours.

Then, the melted soft palm oil mid fraction is gradually cooled to a temperature of 23+/−2 degrees Celsius for over a period of two hours. At 23 degrees Celsius, the soft palm oil mid fraction is subjected to ultrasound treatment. The ultrasound is applied with a power corresponding to 1000 Joules per liter of the soft palm oil mid fraction. After reaching the temperature of 23 degrees Celsius, the soft palm oil mid fraction is kept at constant temperature of 23+/−0.5 degrees Celsius for 18 hours.

After the 18 hours of isothermal crystallization at 23+/−0.5 degrees Celsius, the soft palm oil mid fraction is filtered to obtain an intermediate olein fraction (SPMF-O) and an intermediate stearin fraction (SPMF-S). 25 bars of pressure is applied during the filtering.

Next, the intermediate olein fraction (SPMF-O) is heated to 60 degrees Celsius whereby it is completely melted and kept at this temperature for two hours.

Then, the melted intermediate olein fraction (SPMF-O) is gradually cooled to a temperature of 19.5+/−2 degrees Celsius for over a period of two hours. At 25 degrees Celsius, the intermediate olein fraction (SPMF-O) is subjected to ultrasound treatment. The ultrasound is applied with a power corresponding to 1000 Joules per liter of the intermediate olein fraction (SPMF-O). After reaching the temperature of 19.5 degrees Celsius, the intermediate olein fraction (SPMF-O) is kept at constant temperature of 19.5+/−0.5 degrees Celsius for 17 hours.

After the 17 hours of isothermal crystallization at 19.5 degrees Celsius, the intermediate olein fraction (SPMF-O) is filtered to obtain a final hard palm oil mid fraction (fHPMF-A) and a palm oil olein fraction (POO). 25 bars of pressure is applied during the filtering.

Then, the intermediate stearin fraction (SPMF-S) is heated to 60 degrees Celsius whereby it is completely melted and kept at this temperature for two hours.

Then, the melted intermediate stearin fraction (SPMF-S) is gradually cooled to a temperature of 37+/−2 degrees Celsius for over a period of two hours. After reaching the temperature of 37 degrees Celsius, the intermediate stearin fraction (SPMF-S) is kept at constant temperature of 37+/−0.5 degrees Celsius for 12 hours.

After the 12 hours of isothermal crystallization at 37 degrees Celsius, the intermediate stearin fraction (SPMF-S) is filtered to obtain a second hard palm oil mid fraction (sHPMF-B) and a palm oil stearin fraction (POSt). 25 bars of pressure is applied during the filtering.

Triglyceride content for initial soft palm oil mid fraction (SPMF) as well as the obtained final hard palm oil mid fraction (fHPMF-A), second hard palm oil mid fraction (sHPMF-B), palm oil olein (POO), and palm oil stearin (POSt) is shown in table 1.

TABLE 1

Yield, IV values, triglyceride content, and degree of symmetry for fractions SPMF, fHPMF-A, sHPMF-B, POSt, POO.

| | | Yield [wt %] | IV | POO [wt %] | POP [wt %] | PPP [wt %] | POS [wt %] | SatOSat/ SatSatO | Δ(SatOSat/ SatSatO) [%] |
|---|---|---|---|---|---|---|---|---|---|
| SPMF | Av. | — | 43.7 | 12.8 | 49.9 | 2.1 | 9.3 | 8.6 | — |
| | S.D. | — | 1.5 | 1.0 | 0.8 | 1.0 | 0.4 | 1.1 | — |
| sHPMF-B | Av. | 25 | 34.8 | 4.48 | 68.35 | 1.68 | 10.93 | 6.94 | −19 |
| | S.D. | 3 | 0.4 | 0.40 | 0.68 | 0.29 | 0.38 | 1.13 | 1 |
| fHPMF-A | Av. | 23 | 36.7 | 5.50 | 64.47 | 0.80 | 12.77 | 22.90 | 167 |
| | S.D. | 2 | 0.0 | 0.14 | 0.49 | 0.08 | 0.05 | 3.10 | 25 |
| POSt | Av. | — | 16.5 | 1.2 | 42.9 | 31.7 | 5.9 | — | — |
| | S.D. | — | 0.3 | 0.4 | 2.3 | 2.8 | 0.1 | — | — |
| POO | Av. | — | 56.3 | 24.3 | 30.2 | 0.1 | 6.1 | — | — |
| | S.D. | — | 0.9 | 1.1 | 1.8 | 0.0 | 0.3 | — | — |

Av. = Average, S.D. = Standard Deviation.
Δ(SatOSat/SatSatO) [%] shows the difference in the SatOSat-triglyceride content relative to the SatSatO-triglyceride content when comparing the obtained hard palm oil mid fractions with the initial soft palm oil mid fraction (SPMF).

As can be seen from table 1, the final hard palm oil mid fraction (fHPMF-A) has an even lower relative content of asymmetric SatSatO-triglycerides indicating a highly symmetric fraction in the sense that it has a very high content of symmetric SatOSat-triglycerides.

Also, the second hard palm oil mid fraction (sHPMF-B) has a substantially increased relative content of asymmetric SatSatO-triglycerides.

Example 2—Obtained Compositions and Compositions Based Thereon

Compositions of fat compositions no. 1-8 (Comp. no. 1-8) are shown in table 2. The compositions are obtained by simple mixing of the ingredients. As can be seen, comp. no. 1-2 corresponds to the final hard palm oil mid fraction (fHPMF-A) and the second hard palm oil mid fraction (sHPMF-B) obtained in example 1.

TABLE 2

Recipe for obtaining compositions (Comp.) no. 1-8, using shea stearin, Palm oil stearin (POSt), and hard palm oil mid fractions according to the invention (Comp. no. 1-2). For Comp. no. 6-8, the sum of the content of fHPMF-A, sHPMF-B, shea stearin, and POSt is 100%.

| Comp. no. | Shea stearin | fHPMF-A | sHPMF-B | POSt |
|---|---|---|---|---|
| | | Content [w/w %] | | |
| 1 | — | 100 | — | — |
| 2 | — | — | 100 | — |
| 3 | — | 96 | — | 4 |
| 4 | — | — | 97 | 3 |
| 5 | — | 47.5 | 47.5 | 5 |
| 6 | 40-60 | 40-60 | — | — |
| 7 | 40-60 | — | 40-60 | — |
| 8 | 40-60 | 19-30 | 19-30 | 2-5 |

Palm oil stearin (POSt) is added to comp. no. 3-5, 8 to increase the content of PPP-triglycerides.

Compositions no. 6-8 comprise substantial amounts of hard palm oil mid fraction in combination with shea stearin and thus represents cocoa butter equivalents (CBEs).

Example 3—Obtained Fat Blends

Fat blends 1-4 were obtained as follows.
Fat blend 1 is a 50/50 mixture of fat Comp. no. 1 and 2 from example 2 adjusted with POSt*.
Fat blend 2 is fat Comp. no. 1 from example 2 adjusted with POSt*.
Fat blend 3 is fat Comp. no. 2 from example 2 adjusted with POSt*.
Fat blend 4 (ref) is a standard HPMF (used as a reference).
*Fat blends no. 1-3 are adjusted with POSt to obtain the same content of SatSatSat (see table 3)

The above fat blends are obtained by simple mixing of the ingredients.

The triglyceride composition of fat blends no. 1-3 and 4 (ref) is shown in table 3. As can be seen, fat blend 1 has a SatOSat/SatSatO ratio (ratio between amount of SatOSat-triglycerides and SatSatO-triglycerides) close to that of fat blend 4 (ref). Fat blend 3 has a lower SatOSat/SatSatO ratio, about half of fat blend 1, signifying a lower relative content of symmetric SatOSat-triglycerides, i.e. a higher relative content of asymmetric SatSatO-triglycerides. Therefore, fat blend 3 may be described as having a higher degree of asymmetry.

Fat blend 2 has a higher SatOSat/SatSatO ratio, almost twice of fat blend 4 (ref), signifying a higher relative content of symmetric SatOSat-triglycerides, i.e. a lower relative content of asymmetric SatSatO-triglycerides. Therefore, fat blend 2 may be described as having a higher degree of symmetry.

TABLE 3

Triglyceride composition for fat blends no. 1-4. Fat blend 4 is a reference fat blend.

| | Fat blend no. | | | |
|---|---|---|---|---|
| | 1 | 2 | 3 | 4 (ref) |
| TAG content | Content [w/w %] | | | |
| SatSatSat | 2.6 | 2.6 | 2.6 | 2.8 |
| SatOSat + SatSatO | 80.4 | 80.2 | 80.7 | 82.3 |
| SatOSat/(SatSatO) | 26.9 | 43.7 | 13.6 | 23.4 |
| SatUU | 7.8 | 8.2 | 7.4 | 5.8 |
| UUU | 9.1 | 9.0 | 9.3 | 9.1 |

TAG = Triglyceride. Sat = saturated fatty acid, O = oleic acid, U = unsaturated fatty acid.

Example 4—SFC Values Measured

Solid fat content (SFC) was measured for comp. no. 1-8. SFC is measured with IUPAC 2.150 B.

TABLE 4

Solid fat content (SFC) values for Comp. no. 1-8 at 20, 25, 30, and 35 degrees Celsius.

| Comp. no. | Temperature [degrees Celsius] | | | |
|---|---|---|---|---|
| | 20 | 25 | 30 | 35 |
| | SFC value [%] | | | |
| 1 | 78.9 | 68 | 32 | 0.5 |
| 2 | 81.9 | 68.4 | 33.4 | 0.5 |
| 3 | 80.7 | 68.9 | 40.5 | 0.5 |
| 4 | 82.2 | 68.9 | 38.8 | 1.8 |
| 5 | 81.5 | 68.1 | 41.3 | 2.7 |
| 6 | 71.3 | 65 | 48.5 | 3.8 |
| 7 | 69.7 | 59.7 | 44 | 2.7 |
| 8 | 71.1 | 64 | 48.8 | 3.9 |

POSt = Palm oil stearin. CBE = Cocoa butter equivalent.

Figure 6:
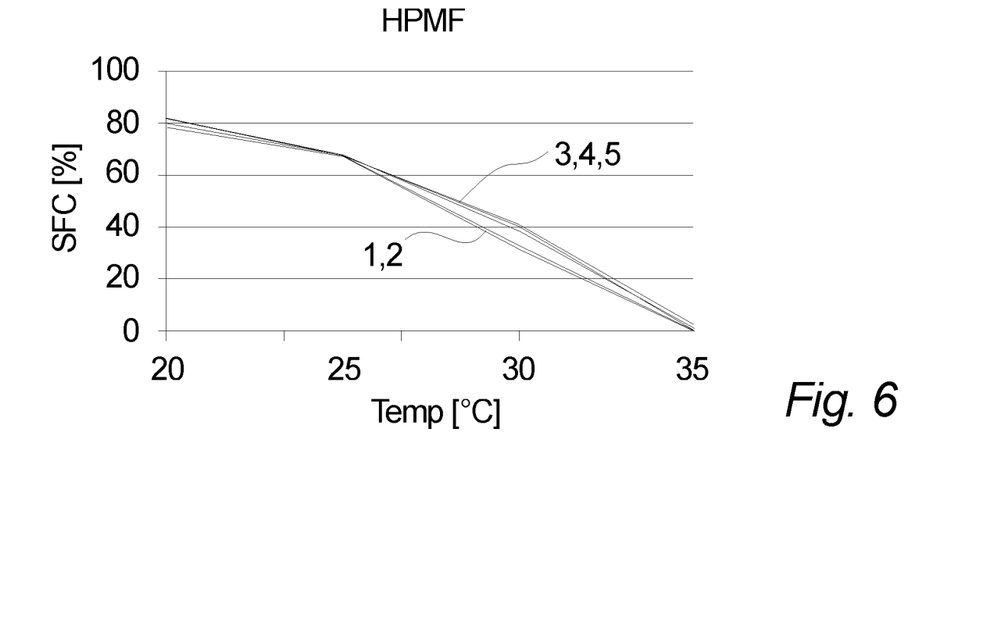
FIG. 6 shows measured SFC values for obtained hard palm oil mid fractions and blends thereof.
Figure 7:
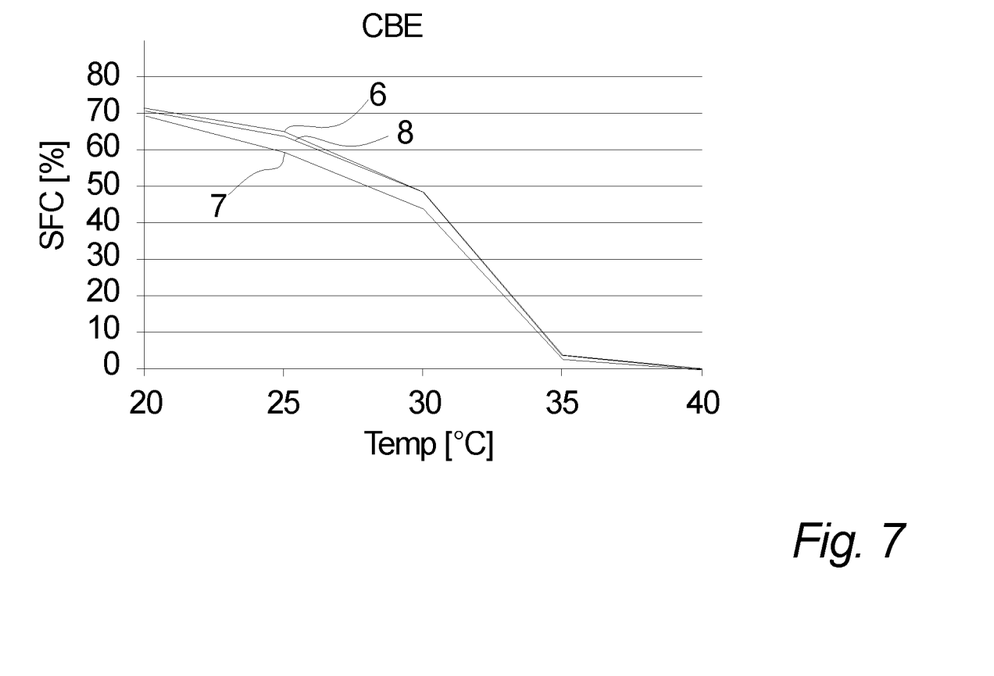
FIG. 7 shows measured SFC values for obtained cocoa butter equivalents based on obtained hard palm oil mid fractions.

The resulting SFC curves of comp. no. 1-5 are shown in FIG. 6, whereas the resulting SFC curves of comp. no. 6-8 are shown in FIG. 7.

As can be seen from FIG. 6, the SFC at 30 degrees Celsius can be adjusted by adding an amount of palm oil stearin (POSt).

Thus, FIG. 6 shows that the final hard palm oil mid fraction (fHPMF-A) and the second hard palm oil mid fraction (sHPMF-B) are quite alike in terms of SFC. Also, it can be seen that adding palm oil stearin (POSt) increases the obtained SFC value at 30 degrees Celsius. Finally, also a 50/50 blend of the final hard palm oil mid fraction (fHPMF-A) and the second hard palm oil mid fraction (sHPMF-B) (comp. no. 5, includes POSt) behaves very similar to its individual main components (comp. no. 1 and 2).

As can be seen from FIG. 7, the CBE made with (fHPMF-A) (comp. no. 6) has higher SFC values at temperatures 25 and 30 degrees Celsius compared to the CBE made with (sHPMF-B) (comp. no. 7). A CBE base on a mixture of (fHPMF-A) and (sHPMF-B) (comp. no. 8), to which POSt is also added, also shows higher SFC values at 25 and 30 degrees Celsius.

The results shown in FIG. 7 demonstrates that the obtained CBE's (comp. no. 6-8) are well behaved with respect to SFC, in the sense that the obtained SFC values are within desired ranges. Also, the fact that the final hard palm oil mid fraction (fHPMF-A) based CBE (Comp. no. 6) has higher SFC values at 25 and 30 degrees Celsius is surprising in view of the content of POP-triglycerides and PPP-triglycerides, but may likely be due be the result of the superior degree of symmetry for the final hard palm oil mid fraction (fHPMF-A).

Example 5.1—Chocolate Manufacturing with Fat Blend 1

Two chocolates, chocolate 1 (milk chocolate) and chocolate 2 (dark chocolate), were made, using fat blend 1 from example 3 as a CBE. Two corresponding reference chocolates, chocolate 1 (ref) and chocolate 2 (ref), were made using the same recipe, except using fat blend 4 (ref) instead of fat blend 1 from example 3.

Thus, all chocolates produced have SatOSat/SatSatO ratios within the ranges of conventional chocolates.

TABLE 5

Compositions of chocolates 1, 1 (ref), 2, and 2 (ref).

| | Choco. 1 | Choco. 1 (ref) | Choco. 2 | Choco. 2 (ref) | Choco. 3 | Choco. 4 |
|---|---|---|---|---|---|---|
| | Content [w/w %] | | | | | |
| Sugar | 40.58 | 40.58 | 53.18 | 53.18 | 53.18 | 53.18 |
| Fat blend 1 | 10 | — | 10 | — | — | — |
| Fat blend 2 | — | — | — | — | — | 10 |
| Fat blend 3 | — | — | — | — | 10 | — |
| Fat blend 4 (ref) | — | 10 | — | 10 | — | — |
| Whole milk powder | 20 | 20 | 0 | 0 | 0 | 0 |
| Cocoa powder (10-12%) | 7 | 7 | 15 | 15 | 15 | 15 |
| Skim milk powder | 5 | 5 | 0 | 0 | 0 | 0 |
| Lecithin | 0.4 | 0.4 | 0.4 | 0.4 | 0.4 | 0.4 |
| Vanillin | 0.02 | 0.02 | 0.02 | 0.02 | 0.02 | 0.02 |
| Cocoa butter | 17 | 17 | 21.4 | 21.4 | 21.4 | 21.4 |
| Total fat content | 33 | 33 | 33 | 33 | 33 | 33 |

Choco. = Chocolate.
Cocoa powder with a fat content of 10-12% by weight was used.

The obtained chocolates were evaluated and no difference between references and chocolates 1 and 2. Particularly, the following have been evaluated finding no differences: Viscosity, tempering, texture, crystallization speed, contraction, and shelf life.

Example 5.2—Chocolate Manufacturing with Fat Blend 2 (Choco. 3)

Chocolate with identical composition as in example 5.1 is made, only exchanging fat blend 1 for fat blend 2.

This blend shows lower viscosity and substantially longer shelf-life compared to the reference (choco 2 (ref)). Other factors: tempering, texture, crystallization speed, contraction, are similar.

The shelf-life test has been carried out at 20° C. on 100 g molded tablets with 20% hazelnuts.

TABLE 6

Shelf life of chocolates 2-4.

| | Choco. 2 (ref) | Choco. 3 | Choco. 4 |
|---|---|---|---|
| Weeks until bloom | 4 | 7 | 4 |

Example 5.3—Chocolate Manufacturing with Fat Blend 3 (Choco. 4)

Chocolate with identical composition as in example 5.1 is made, only exchanging fat blend 1 for fat blend 3.

This blend shows lower viscosity compared to the reference (choco 2 (ref)). Other factors: tempering, texture, crystallization speed, contraction, are similar.

FIGURE REFERENCES

SPMF. Soft palm oil mid fraction
mSPMF. Melted soft palm oil mid fraction
ssSPMF. Supersaturated soft palm oil mid fraction
fHPMF-A. Final hard palm oil mid fraction
sHPMF-B. Second hard palm oil mid fraction
SPMF-O. Intermediate olein fraction mSPMF-O. Melted intermediate olein fraction
ssSPMF-O. Supersaturated intermediate olein fraction
SPMF-S. Intermediate stearin fraction
mSPMF-S. Melted intermediate stearin fraction
ssSPMF-S. Supersaturated intermediate stearin fraction
POSt. Palm oil stearin
SOF. Super olein fraction
FDF. First dry fractionation
SDF. Second dry fractionation
TDF. Third dry fractionation
PDF. Preceding dry fractionation
POO. Palm oil olein
CO1. First cooling
CO2. Second cooling
CO3. Third cooling
CRY1. First crystallization
CRY2. Second crystallization
CRY3. Third crystallization
FLT1. First filtering
FLT2. Second filtering
FLT3. Third filtering
IN1. First input
IN2. Second input
IN3. Third input
MLT1. First melting
MLT2. Second melting
MLT3. Third melting
SL1. First slurry
SL2. Second slurry
SL3. Third slurry
US1. First ultrasonic treatment
US2. Second ultrasonic treatment

The invention claimed is:

1. A process for dry fractionation of a soft palm oil mid fraction into a final hard palm oil mid fraction, the process comprising:
providing the soft palm oil mid fraction;
using the soft palm oil mid fraction as a first input to a first dry fractionation to obtain an intermediate olein fraction and an intermediate stearin fraction;
using the intermediate olein fraction as a second input to an ultrasound assisted second dry fractionation to obtain the final hard palm oil mid fraction and a palm oil olein fraction;
wherein the ultrasound assisted second dry fractionation comprises subjecting at least a part of the second input to ultrasonic treatment; and
wherein the final hard palm oil mid fraction has a weight ratio of SatOSat-triglycerides/SatSatO-triglycerides above 15.

2. The process of claim 1, wherein the first dry fractionation is an ultrasound assisted first dry fractionation, comprising subjecting at least part of the first input to ultrasonic treatment.

3. The process of claim 1, wherein the ultrasound assisted second dry fractionation comprises cooling the second input to obtain a supersaturated second input, prior to the ultrasonic treatment.

4. The process of claim 3, wherein the ultrasound assisted second dry fractionation comprises crystallization of the supersaturated second input, at least a part of which having been subjected to the ultrasonic treatment.

5. The process of claim 4, wherein the crystallization is performed in a crystallizer, and where the ultrasonic treatment is performed external to the crystallizer.

6. The process of claim 4, wherein the crystallization is performed in a crystallizer, and where the ultrasonic treatment is performed in the crystallizer.

7. The process of claim 4, wherein the crystallization is performed in a crystallizer, and where the cooling is performed in the crystallizer.

8. The process of claim 4, wherein the crystallization is performed in a crystallizer, and where the cooling is performed external to the crystallizer.

9. The process of claim 1, wherein the first dry fractionation comprises:
melting, in a first melting step, the soft palm oil mid fraction to obtain a melted soft palm oil mid fraction;
cooling, in a first cooling step, the melted soft palm oil mid fraction to obtain a supersaturated soft palm oil mid fraction;
crystallization, in a first crystallization step, of the supersaturated soft palm oil mid fraction to obtain a first slurry; and
filtering, in a first filtration step, the first slurry to obtain the intermediate olein fraction and the intermediate stearin fraction.

10. The process according to claim 9, wherein the first dry fractionation further comprises subjecting, in an ultrasonic treatment, at least a part of the supersaturated soft palm oil mid fraction to ultrasound.

11. The process of claim 9, wherein the ultrasound assisted second dry fractionation comprises:
melting, in a second melting step, the intermediate olein fraction to obtain a melted intermediate olein fraction;
cooling, in a second cooling step, the melted intermediate olein fraction to obtain a supersaturated intermediate olein fraction;
subjecting, in an ultrasonic treatment, at least a part of the supersaturated intermediate olein fraction to ultrasound;
crystallization, in a second crystallization step, of the supersaturated intermediate olein fraction having at least partly been subjected to ultrasonic treatment to obtain a second slurry; and
filtering, in a second filtration step, the second slurry to obtain the final hard palm oil mid fraction and the palm oil olein fraction.

12. The process of claim 1, wherein the palm oil olein fraction is used to obtain a further soft palm oil mid fraction.

13. The process of claim 1, wherein the process comprises a preceding dry fractionation of the palm oil olein to obtain a soft palm oil mid fraction and a super olein fraction.

14. The process of claim 1, wherein the first dry fractionation and the second dry fractionation is performed using the same dry fractionation system.

15. The process of claim 1, wherein the ultrasonic treatment has a duration of at least 5 minutes.

16. The process of claim 1, wherein the ultrasonic treatment is performed on at least 5% by weight of the intermediate olein fraction.

17. The process of claim 1, wherein the ultrasonic treatment is performed at an average frequency of ultrasound of between 5 and 200 KHz.

18. The process of claim 1, wherein the ultrasonic treatment is performed having an acoustic energy of at least 50 Joules per Liter of the second input.

19. The process of claim 9, wherein the cooling has a duration of at least 2 hours after reaching a supersaturation threshold.

20. The process of claim 1, wherein the final hard palm oil mid fraction is obtained in an amount of 15 to 50% by weight of the soft palm oil mid fraction.

21. The process of claim 11, wherein the process further comprises using the intermediate stearin fraction as a third input to a third dry fractionation to obtain a second hard palm oil mid fraction and a palm oil stearin fraction.

22. The process according to claim 21, wherein the third dry fractionation comprises:
melting, in a third melting step, the intermediate stearin fraction to obtain a melted intermediate stearin fraction;
cooling, in a third cooling step, the melted intermediate stearin fraction to obtain a supersaturated intermediate stearin fraction;
crystallization, in a third crystallization step, of the supersaturated intermediate stearin fraction to obtain a third slurry; and
filtering the third slurry to obtain the second hard palm oil mid fraction and the palm oil stearin fraction.

23. A final hard palm oil mid fraction comprising:
POP-triglycerides in an amount of at least 62 percent by weight of the final hard palm oil mid fraction; and
PPP-triglycerides in an amount of less than 2 percent by weight of the final hard palm oil mid fraction;
wherein the final hard palm oil mid fraction has an iodine value below 38 and a weight ratio of SatOSat-triglycerides/SatSatO-triglycerides above 15.

* * * * *

UNITED STATES PATENT AND TRADEMARK OFFICE
CERTIFICATE OF CORRECTION

| | | |
|---|---|---|
| PATENT NO. | : 12,091,633 B2 | Page 1 of 1 |
| APPLICATION NO. | : 17/267097 | |
| DATED | : September 17, 2024 | |
| INVENTOR(S) | : Jeppe Lindegaard Hjorth | |

It is certified that error appears in the above-identified patent and that said Letters Patent is hereby corrected as shown below:

On the Title Page

Item (57) Abstract, Line 3, "solf" should read as --soft--.

In the Claims

Claim 4, Column 21, Line 63, "which having" should read as --which has--.

Signed and Sealed this
Nineteenth Day of November, 2024

Katherine Kelly Vidal
*Director of the United States Patent and Trademark Office*